(12) United States Patent
Buisine

(10) Patent No.: US 9,067,869 B2
(45) Date of Patent: Jun. 30, 2015

(54) METHOD FOR PREPARING DIFLUOROACETONITRILE AND THE DERIVATIVES THEREOF

(75) Inventor: Olivier Buisine, Saint-Genis-Laval (FR)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 14/003,118

(22) PCT Filed: Mar. 8, 2012

(86) PCT No.: PCT/EP2012/053959
§ 371 (c)(1),
(2), (4) Date: Sep. 18, 2013

(87) PCT Pub. No.: WO2012/120067
PCT Pub. Date: Sep. 13, 2012

(65) Prior Publication Data
US 2014/0012033 A1    Jan. 9, 2014

(30) Foreign Application Priority Data
Mar. 9, 2011 (FR) .................. 11 00708

(51) Int. Cl.
C07C 253/14 (2006.01)
C07C 51/08 (2006.01)

(52) U.S. Cl.
CPC .............. C07C 253/14 (2013.01); C07C 51/08 (2013.01)

(58) Field of Classification Search
USPC ........................................ 558/342
See application file for complete search history.

(56) References Cited

U.S. PATENT DOCUMENTS

| 2,912,455 | A | * | 11/1959 | Smiley ..................... 558/342 |
| 2,939,878 | A | * | 6/1960 | Ruh et al. ................ 558/348 |
| 3,116,318 | A | * | 12/1963 | Fierce et al. ............. 558/336 |
| 3,206,499 | A | * | 9/1965 | Ham ........................ 558/342 |
| 3,234,267 | A | * | 2/1966 | Vogh ....................... 558/342 |
| 3,330,628 | A | * | 7/1967 | Brown ..................... 423/276 |
| 6,153,784 | A | * | 11/2000 | Kneuper et al. ......... 558/456 |
| 8,242,311 | B2 | * | 8/2012 | Lui et al. ................. 564/493 |
| 2005/0148649 | A1 | | 7/2005 | Billen et al. |
| 2006/0122399 | A1 | | 6/2006 | Gonzalez et al. |
| 2010/0016612 | A1 | * | 1/2010 | Umetani et al. ........ 548/374.1 |
| 2010/0312002 | A1 | | 12/2010 | Lui et al. |
| 2011/0166385 | A1 | | 7/2011 | Buisine et al. |

FOREIGN PATENT DOCUMENTS

| CN | 101006092 A | 7/2007 |
| CN | 100377645 C | 4/2008 |
| SU | 290697 A1 | 12/1975 |
| WO | WO 2010003986 A1 | 1/2010 |
| WO | WO 2010142377 A1 | 12/2010 |

* cited by examiner

Primary Examiner — Nyeemah A Grazier
(74) Attorney, Agent, or Firm — Beatrice C. Ortego

(57) ABSTRACT

The present invention relates to a method for preparing difluoracetonitrile and the derivatives thereof. The method for preparing difluoroacetonitrile according to the invention is characterized in that it includes reacting halogenodifluoromethane and a source of cyanide anions in an alkaline medium. The invention also relates to the use of difluoroacetonitrile as an intermediate in the manufacture of difluoroacetic acid and the salts, esters, or amide thereof.

21 Claims, No Drawings

METHOD FOR PREPARING DIFLUOROACETONITRILE AND THE DERIVATIVES THEREOF

The present application is a U.S. national stage entry under 35 U.S.C. §371 of International Application No. PCT/EP2012/053959 filed Mar. 8, 2012, which claims priority to French Application No. 11.00708 filed on Mar. 9, 2011, the whole content of this application being herein incorporated by reference for all purposes.

The present invention relates to a process for preparing difluoroacetonitrile and derivatives thereof.

More specifically, the invention relates to the preparation of difluoroacetonitrile and derivatives thereof, such as acid, salt, ester or amide derivatives.

Difluoroacetonitrile is a fluorinated organic compound that is used as a production intermediate in various fields of application, in particular in the agrochemical and pharmaceutical fields.

Thus, it is desirable to have a preparation process that is capable of being carried out on an industrial scale.

A process has now been found, and it is this which constitutes the subject of the present invention, for preparing difluoroacetonitrile, characterized in that it comprises the reaction of a halodifluoromethane and of a source of cyanide anions, in a basic medium.

The starting substrate that takes part in the process of the invention corresponds to the following formula:

$$HXCF_2 \qquad (I)$$

in said formula, X represents a chlorine, bromine or iodine atom.

In the formula (I), X preferably represents a chlorine or bromine atom.

More preferably still, X represents a chlorine atom since the corresponding compound of formula (I) is chlorodifluoromethane (or R22), which is a raw material of choice since it is manufactured on a large scale.

This compound is available at ambient temperature and atmospheric pressure in gas form.

The expression "source of cyanide anions" is understood to mean a salt that provides a $CN^-$ anion.

As examples of salts suitable for the process of the invention, mention may be made of the salts of alkali or alkaline-earth metals.

The expressions "alkali metal" and "alkaline-earth metal" refer to the elements from groups (IA) and (IIA) of the Periodic Table of the Elements.

In the present text, reference is made to the Periodic Table of the Elements published in the Bulletin de la Société Chimique de France, no. 1 (1966).

For obvious economic reasons, sodium cyanide and potassium cyanide are more particularly chosen. However, the invention does not exclude any other source of cyanide anions.

The concentration of the cyanide source expressed as $CN^-$ may represent from 5% to 40% of the weight of water.

The amount of cyanide source introduced is preferably chosen such that the ratio between the number of moles of cyanide source expressed as $CN^-$ and the number of moles of halodifluoromethane varies between 0.8 and 2.0 and preferably between 0.9 and 1.0.

In accordance with the process of the invention, the cyanation reaction is carried out in the presence of a base.

The characteristic of the base is that it has a $pK_a$ at least greater than or equal to 10, preferably between 10 and 14.

The $pK_a$ is defined as being the ionic dissociation constant of the acid/base pair, when water is used as solvent.

For the choice of a base having a $pK_a$ as defined by the invention, reference may be made, inter alia, to the *Handbook of Chemistry and Physics,* 66th edition, p. D-161 and D-162.

According to the process of the invention, the cyanation reaction is carried out in an aqueous medium containing, in solution, a basic agent, and more particularly alkali metal or alkaline-earth metal bases, among which mention may be made of hydroxides such as sodium, potassium or lithium hydroxide and barite; alkali metal alcoholates such as sodium or potassium methylate, ethylate, isopropylate and t-butylate; sodium or potassium carbonates or bicarbonates, and generally the salts of alkali metal or alkaline-earth metal bases and weak acids.

For economic reasons, use is made of sodium hydroxide or potassium hydroxide.

Advantageously, use is made of an aqueous solution of alkali metal hydroxide having a concentration generally between 5% and 50% by weight. The concentration of the starting solution is not critical. However, it is preferred to use a more concentrated solution having a concentration that varies between 30% and 50% by weight.

It is also possible to add, separately, the base in solid form and the water.

The amount of base preferably used is such that the ratio between the number of moles of base expressed as $OH^-$ and the number of moles of chlorodifluoromethane preferably varies between 0.05 and 0.5, and more preferably between 0.05 and 0.2.

In accordance with the process of the invention, the reaction is preferably carried out in an aqueous medium, although a reaction solvent is not excluded.

The water is generally provided by the basic solution.

The temperature of the cyanation reaction is chosen so that it is sufficient to enable the reaction to be carried out.

The temperature of the reaction is preferably chosen to be between 20° C. and 150° C. and more preferably between 50° C. and 120° C.

It generally takes place under autogenous pressure of the reactants and products: the pressure generally lies between 10 and 150 bar (absolute).

It is optionally possible to carry out the reaction preferably under an atmosphere of an inert gas which may be nitrogen or a noble gas, preferably argon: nitrogen is preferred, in particular considering its reduced cost.

From a practical point of view, the process according to the invention is simple to implement.

The source of cyanide, the basic solution (or base+water) are mixed, then the halodifluoromethane is introduced into this reaction medium.

The whole mixture is then brought to the reaction temperature, chosen from within the aforementioned range, which temperature is maintained for example for between 2 and 8 hours.

At the end of the reaction, a two-phase medium is obtained that comprises the difluoroacetonitrile.

More specifically, at ambient temperature (15° C. to 25° C.), the aqueous phase comprises the base and optionally the excess of the cyanide source in aqueous solution and the organic phase comprises the difluoroacetonitrile and optionally the excess of the halodifluoromethane.

The difluoroacetonitrile is recovered, for example, by separating the aqueous and organic phases by decantation and conventional distillation of the organic phase thus making it possible to obtain the difluoroacetonitrile.

Another method of separating the difluoroacetonitrile consists in carrying out the distillation of the medium resulting from the reaction without having first carried out a decantation.

The distillation step is designed to obtain:
as distillation bottoms, the water, the base and optionally the excess of the source of cyanide anions,
and as distillation overhead, a gas phase comprising firstly the excess of the halodifluoromethane then the expected difluoroacetonitrile.

The distillation is carried out at a temperature in the boiler that is chosen so that the temperature is sufficient to obtain, at the top of the column, the boiling point of difluoroacetonitrile.

The distillation is preferably carried out under atmospheric pressure. However, a pressure slightly lower or higher than atmospheric pressure is also possible.

The distillation is performed using a conventional distillation column.

When the temperature at the top of the column is between 20° C. and 22° C., at atmospheric pressure, a gas phase constituted of difluoroacetonitrile is recovered at the top of the column.

This gas phase is cooled and converted to liquid form by cooling to a temperature, for example, between −10° C. and 15° C., preferably between 0° C. and 10° C.

This operation is carried out by passing through a condenser, which is a conventional device, for example a tubular heat exchanger fed with water or with a fluid maintained at a temperature lower than the chosen cooling temperature, generally 5° C. to 10° C. lower.

The condensed flow consists of the difluoroacetonitrile and a fraction of this flow may be introduced, laterally at the top of the distillation column, in order to ensure the reflux of the column.

Another subject of the invention consists in using the difluoroacetonitrile prepared previously as a production intermediate.

Thus, the invention also relates to a process for preparing difluoroacetic acid, and the salts, esters or amide thereof, characterized in that it comprises a first step of preparing difluoroacetonitrile from a halodifluoromethane in accordance with the process described previously, followed by a hydrolysis operation.

The process of the invention therefore makes it possible to prepare the derivatives corresponding to the following formula:

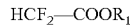   HCF$_2$—COOR$_1$   (II)

in said formula:
R$_1$ represents:
a hydrogen atom,
a substituted or unsubstituted hydrocarbon-based group, which may be an alkyl or cycloalkyl group,
a metal cation,
an amino group.

According to a first variant of the invention, difluoroacetic acid is prepared, which corresponds to the formula (II) in which R$_1$ represents a hydrogen atom.

The process for preparing difluoroacetic acid comprises the hydrolysis of the difluoroacetonitrile obtained, in an acid medium.

The amount of water used in this hydrolysis step is generally such that the ratio between the number of moles of water and the number of moles of difluoroacetonitrile is between 2 and 5.

The acidification is carried out using a strong acid having a pK$_a$ of less than or equal to 2.

The pK$_a$ is defined as being the ionic dissociation constant of the acid/base pair, when water is used as solvent.

A strong acid is chosen that advantageously does not have an oxidizing character. Thus, nitric acid is not preferred. Use is more preferably made of sulfuric, hydrochloric or phosphoric acid.

Sulfuric acid is preferably chosen.

Use is advantageously made of a concentrated solution of strong acid.

More particularly, the commercial forms of acids are used.

Mention may in particular be made of the solutions of 95% or 98% by weight sulfuric acid, of 37% by weight hydrochloric acid, and of 95-100% by weight phosphoric acid.

The amount of strong acid used is such that the ratio between the number of moles of acid expressed as H$^+$ ions and the number of moles of difluoroacetonitrile varies between 1 and 5, preferably between 1 and 2.

The hydrolysis operation is advantageously carried out at a temperature between 100° C. and 150° C.

It is generally performed under autogenous pressure of the reactants and products.

It is also possible to establish an inert atmosphere, preferably a nitrogen atmosphere.

According to one practical embodiment of the invention, the difluoroacetonitrile and the acid solution are mixed.

The reaction mixture is brought to the chosen hydrolysis temperature and this temperature is maintained for a duration that varies, for example, between 8 and 12 hours.

At the end of the hydrolysis, the temperature is lowered, for example between 20° C. and 80° C.

A medium is obtained that comprises difluoroacetic acid, water and an ammonium salt, the anion of which corresponds to that of the acid used.

Since the hydrolysis is preferably carried out using an aqueous solution of sulfuric acid, the ammonium sulfate formed is thus found in the aqueous phase.

The difluoroacetic acid is recovered by any conventional means, for example by distillation.

According to a second variant of the invention, a difluoroacetic acid salt is prepared, which corresponds to the formula (II) in which R$_1$ represents a metal cation.

Mention may more particularly be made, preferably, of an alkali metal or alkaline-earth metal cation.

As more specific examples of cations, mention may be made of alkali metal cations, preferably lithium, sodium, potassium or caesium cations; and alkaline-earth metal cations, preferably magnesium, calcium or barium cations.

In the aforementioned list, the preferred metal cations are sodium or potassium cations.

The process for preparing a difluoroacetic acid salt comprises the hydrolysis of the difluoroacetonitrile obtained, in a basic medium.

The amount of water used in this hydrolysis step is generally such that the ratio between the number of moles of water and the number of moles of difluoroacetonitrile is between 2 and 5.

The base that provides the cation R$_1$ is chosen, and mention may more particularly be made of alkali metal or alkaline-earth metal hydroxides.

Preferably, sodium hydroxide or potassium hydroxide is chosen.

Use is especially made of sodium hydroxide or potassium hydroxide solutions having a concentration that varies between 30% and 50% by weight.

The amount of base preferably used is such that the ratio between the number of moles of base expressed as OH⁻ ions and the number of difluoroacetonitrile varies between 1 and 10, preferably between 2 and 5.

The hydrolysis operation is advantageously carried out at a temperature between 100° C. and 130° C., for a duration that varies, for example, between 4 and 12 hours, preferably between 6 and 10 hours.

It is generally performed at atmospheric pressure but under autogenous pressure of the reactants.

It is also possible to establish an inert atmosphere, preferably a nitrogen atmosphere.

According to one practical embodiment of the invention, the difluoroacetonitrile and the basic solution are mixed.

The reaction mixture is brought to the chosen hydrolysis temperature and this temperature is maintained for a duration that varies, for example, between 8 and 12 hours.

At the end of the hydrolysis, the pressure is reduced to atmospheric pressure.

The medium obtained comprises the difluoroacetic acid salt and ammonia in solution, it being possible for the latter to be eliminated in particular by air or nitrogen entrainment.

It is possible to recover the difluoroacetic acid salt from the reaction mixture in particular by the separation technique described in WO 2010/03986.

Another method of preparing a salt of difluoroacetic acid comprises the reaction of a halodifluoromethane and of a source of cyanide anions, in the presence of the amount of base necessary both for carrying out the cyanation reaction and the hydrolysis reaction.

The reactants used are as described previously in the difluoroacetonitrile preparation step.

The amount of cyanide source introduced is preferably chosen such that the ratio between the number of moles of cyanide source expressed as CN⁻ and the number of moles of halodifluoromethane varies between 0.8 and 2.0 and preferably between 0.9 and 1.0.

The amount of base preferably used is such that the ratio between the number of moles of base expressed as OH⁻ and the number of moles of chlorodifluoromethane varies between 2 and 5 and more preferably lies close to 2.

The reaction is advantageously carried out in an aqueous medium, the water generally being provided by the basic solution.

The temperature of the reaction is preferably chosen to be between 100° C. and 120° C.

It generally takes place under autogenous pressure of the reactants and products: the pressure generally lies between 10 and 150 bar (absolute).

It is optionally possible to carry out the reaction under an inert gas atmosphere.

From a practical point of view, the process according to the invention is simple to implement.

An autoclave is charged with the cyanide source and the basic solution (or base+water). The autoclave is closed and the halodifluoromethane is introduced.

The whole mixture is then brought to the reaction temperature, chosen to be between 120° C. and 130° C., which temperature is maintained for example for between 10 and 20 hours.

At the end of the reaction, the pressure is brought back to atmospheric pressure and the temperature to ambient temperature.

The difluoroacetic acid salt is recovered in the aqueous phase.

According to a third variant of the invention, difluoroacetic acid esters are prepared, which correspond to the formula (II)

in which $R_1$ represents a substituted or unsubstituted hydrocarbon-based group which may be an alkyl, cycloalkyl or aralkyl group.

Within the context of the invention, the term "alkyl" is understood to mean a linear or branched hydrocarbon-based chain having from 1 to 15 carbon atoms and preferably 1 or 2 to 10 carbon atoms.

Examples of preferred alkyl groups are especially methyl, ethyl, propyl, isopropyl, butyl, isobutyl and t-butyl.

The term "cycloalkyl" is understood to mean a monocyclic cyclic hydrocarbon-based group comprising from 3 to 8 carbon atoms, preferably a cyclopentyl or cyclohexyl group.

The term "aralkyl" is understood to mean a linear or branched hydrocarbon-based group bearing a $C_7$-$C_{12}$ monocyclic aromatic ring, preferably a benzyl ring, the aliphatic chain comprising 1 or 2 carbon atoms.

It should be noted that in these groups, one or more hydrogen atoms may be replaced by a substituent (for example a halogen).

In particular, the hydrocarbon-based chain may preferably bear one or more fluorine atoms.

Thus, $R_1$ may represent a fluoroalkyl or perfluoroalkyl group comprising from 1 to 10 carbon atoms and from 1 to 21 fluorine atoms, preferably from 3 to 21 fluorine atoms.

The process for preparing difluoroacetic acid esters comprises the hydrolysis of the difluoroacetonitrile obtained, in an acid medium and in the presence of an alcohol $R_1$—OH.

The amount of water used in this hydrolysis step is generally such that the ratio between the number of moles of water and the number of moles of difluoroacetonitrile is between 1 and 5.

The amount of alcohol used is preferably chosen so that the ratio between the number of moles of alcohol and the number of moles of difluoroacetonitrile varies between 1 and 3, preferably between 1 and 2.

The acidification is carried out using a strong acid having a $pK_a$ of less than or equal to 2.

The $pK_a$ is defined as being the ionic dissociation constant of the acid/base pair, when water is used as solvent.

A strong acid is chosen that advantageously does not have an oxidizing character. Thus, nitric acid is not preferred. Use is more preferably made of sulfuric, hydrochloric or phosphoric acid.

Sulfuric acid is preferably chosen.

Use is advantageously made of a concentrated solution of strong acid.

More particularly, the commercial forms of acids are used.

Mention may in particular be made of the solutions of 95% or 98% by weight sulfuric acid, of 37% by weight hydrochloric acid, and of 95-100% by weight phosphoric acid.

The amount of strong acid used is such that the ratio between the number of moles of acid expressed as H⁺ ions and the number of difluoroacetonitrile varies between 1 and 5, preferably between 1 and 2.

The hydrolysis operation is advantageously carried out at a temperature between 100° C. and 150° C.

It is generally performed at atmospheric pressure but under autogenous pressure of the reactants.

It is also possible to establish an inert atmosphere, preferably a nitrogen atmosphere.

According to one practical embodiment of the invention, the difluoroacetonitrile, the acid solution and the alcohol are mixed.

The reaction mixture is brought to the chosen hydrolysis temperature and this temperature is maintained for a duration that varies, for example, between 8 and 12 hours.

At the end of the hydrolysis, the temperature is lowered, for example between 20° C. and 80° C.

The corresponding iminoester is obtained, which is subjected to a hydrolysis operation.

The amount of water used in this hydrolysis step is generally such that the ratio between the number of moles of water and the number of moles of difluoroacetonitrile is between 1 and 5, preferably between 1 and 3.

The hydrolysis is advantageously carried out at a temperature between 50° C. and 100° C.

A two-phase medium is obtained that comprises an organic phase consisting of the difluoroacetic acid ester and an aqueous phase comprising water and an ammonium salt, the anion of which corresponds to that of the acid used.

Since the hydrolysis is preferably carried out using an aqueous solution of hydrochloric acid, the ammonium chloride formed is thus found in the aqueous phase.

The aqueous and organic phases are separated according to conventional liquid/liquid separation techniques, for example decantation or centrifugation.

The difluoroacetic acid ester that constitutes the organic phase is recovered.

According to a fourth variant of the invention, difluoroacetamide is prepared, which corresponds to the formula (II) in which $R_1$ represents an amino group.

The process for preparing difluoroacetamide comprises the controlled hydrolysis of the difluoroacetonitrile obtained, in an acid medium.

The amount of water used in this hydrolysis step is generally such that the ratio between the number of moles of water and the number of moles of difluoroacetonitrile is between 1 and 5.

The acidification is carried out using a strong acid having a $pK_a$ of less than or equal to 2.

The $pK_a$ is defined as being the ionic dissociation constant of the acid/base pair, when water is used as solvent.

A strong acid is chosen that advantageously does not have an oxidizing character. Thus, nitric acid is not preferred. Use is more preferably made of sulfuric, hydrochloric or phosphoric acid.

Sulfuric acid is preferably chosen.

Use is advantageously made of a concentrated solution of strong acid.

More particularly, the commercial forms of acids are used.

Mention may in particular be made of the solutions of 95% or 98% by weight sulfuric acid, of 37% by weight hydrochloric acid, and of 95-100% by weight phosphoric acid.

The amount of strong acid used is such that the ratio between the number of moles of acid expressed as $H^+$ ions and the number of moles of difluoroacetonitrile varies between 0.05 and 1, preferably between 0.05 and 0.2.

The hydrolysis operation is advantageously carried out at a temperature between 100° C. and 150° C.

It is generally performed under autogenous pressure of the reactants.

It is also possible to establish an inert atmosphere, preferably a nitrogen atmosphere.

According to one practical embodiment of the invention, the difluoroacetonitrile and the acid solution are mixed.

The reaction mixture is brought to the chosen hydrolysis temperature and this temperature is maintained for a duration that varies, for example, between 1 and 2 hours.

At the end of the hydrolysis, the temperature is lowered, for example between 20° C. and 80° C.

A two-phase medium is obtained that comprises an aqueous phase comprising the excess water and acid introduced and a solid mainly consisting of difluoroacetamide.

The difluoroacetamide is separated according to conventional solid/liquid separation techniques, preferably by filtration.

It may optionally be purified according to customary techniques such as recrystallization or extraction.

The process of the invention is advantageously carried out in equipment capable of withstanding the corrosion of the reaction medium.

For this purpose, materials are chosen for the part in contact with the reaction medium that are corrosion-resistant, such as the alloys based on molybdenum, chromium, cobalt, iron, copper, manganese, titanium, zirconium, aluminum, carbon and tungsten, sold under the HASTELLOY® brands or the alloys of nickel, chromium, iron and manganese to which copper and/or molybdenum are added sold under the name INCONEL® and more particularly the HASTELLOY C 276 or INCONEL 600, 625 or 718 alloys.

Stainless steels may also be chosen, such as austenitic steels [Robert H. Perry et al., *Perry's Chemical Engineers' Handbook*, Sixth Edition (1984), pages 23-44] and more particularly the 304, 304 L, 316 or 316 L stainless steels. A steel having a nickel content of at most 22% by weight, preferably of between 6% and 20% and more preferably of between 8% and 14%, is used.

The 304 and 304 L steels have a nickel content that varies between 8% and 12%, and the 316 and 316 L steels have a nickel content that varies between 10% and 14%.

More particularly, 316 L steels are chosen.

Use may also be made of equipment constituted of or coated with a polymeric compound resistant to the corrosion of the reaction medium. Mention may especially be made of materials such as PTFE (polytetrafluoroethylene or Teflon) or PFA (perfluoroalkyl resins) or high-density polyethylene. It will not be outside the scope of the invention to use an equivalent material.

As other materials capable of being suitable for being in contact with the reaction medium, mention may also be made of the glass-lined steels and the derivatives of graphite.

The process of the invention may be carried out continuously or in batch mode.

It is particularly advantageous since it is a simple process which uses a common reactant and which makes it possible to obtain difluoroacetic acid, and the salts, esters or amide thereof.

Exemplary embodiments of the invention are given hereinbelow. These examples are given by way of illustration and non-limitingly.

In the examples, the yield obtained is defined.

The reaction yield (RY) corresponds to the ratio between the number of moles of product formed and the number of moles of substrate employed.

EXAMPLE 1

Preparation of Difluoroacetonitrile

In an autoclave having a volume of 200 ml equipped with a Rushton-type stirrer, sodium cyanide (2.57 g, 52.4 mmol) and sodium hydroxide (0.4 g, 10.5 mmol) are dissolved in 22 ml of water.

The autoclave is closed and chlorodifluoromethane is added under pressure (9 g, 105 mmol).

The pressure obtained at ambient temperature is 12.8 bar relative pressure.

The temperature is then brought to 95° C. for a duration of two hours, then brought back to a temperature of 40° C.

The autoclave is brought back to atmospheric pressure.

The gases are collected then analyzed by gas chromatography.

A total mass of 6.3 g is obtained, composed of chlorodifluoromethane (3.6 g) and difluoroacetonitrile (2.7 g).

The yield is 67%.

EXAMPLE 2

Preparation of Sodium Difluoroacetate

The difluoroacetonitrile is placed in a 100 ml autoclave equipped with a Rushton-type stirrer, containing 30 g of a 30% (230 mmol) sodium hydroxide solution.

The temperature is lowered to 5° C. and the difluoroacetonitrile (m=9.8 g, 0.127 mol) is poured at this temperature.

The temperature of the medium is brought to 115° C. for a duration of 13 h, then brought back to ambient temperature.

The autoclave is brought back to atmospheric pressure.

The concentration of sodium difluoroacetate in the aqueous solution obtained is 11.6% by weight (analysis by $^{19}$F NMR), which corresponds to a mass of 2.63 g of sodium difluoroacetate, i.e. 87% of the theoretical value.

EXAMPLE 3

Preparation of Sodium Difluoroacetate

In an autoclave having a volume of 200 ml equipped with a Rushton-type stirrer, sodium cyanide (2.6 g, 0.053 mmol) and sodium hydroxide (4.2 g, 0.13 mol) are dissolved in 25 ml of water.

The autoclave is closed and chlorodifluoromethane is introduced under pressure (9 g, 105 mmol).

The temperature is then brought to 117° C. for a duration of 17 hours, then brought back to ambient temperature.

The autoclave is brought back to atmospheric pressure.

The aqueous solution obtained (29 g) contains 12.5% by weight of sodium difluoroacetate, which is equivalent to 3.64 g of pure sodium difluoroacetate, i.e. 54% of the theoretical value.

EXAMPLE 4

Preparation of Ethyl Difluoroacetate

A mixture of 98% sulfuric acid (25.5 g, 0.259 mol), water (9.35 g, 0.52 mol) and ethanol (9 g; 0.19 mol) is introduced into a glass reactor equipped with a stirrer.

The temperature is lowered to 10° C. and the difluoroacetonitrile (10 g, 0.13 mol) is introduced at this temperature.

The temperature is then brought to 120° C. for a duration of 14 h, then brought back to ambient temperature.

The medium is decanted and the upper phase is recovered.

10.5 g of ethyl difluoroacetate that is 87% by weight pure are obtained, which corresponds to a mass of 9.2 g of pure ethyl difluoroacetate (the yield is 57%).

The crude ethyl difluoroacetate obtained is purified by distillation at atmospheric pressure.

The fraction that has a boiling point between 75° C. and 77° C. is collected.

5.5 g of ethyl difluoroacetate, with a purity determined by gas chromatography of greater than 98% by weight, are obtained.

The invention claimed is:

1. A process for preparing difluoroacetonitrile, comprising a reaction of a halodifluoromethane and of a source of cyanide anions, in a basic aqueous medium.

2. The process as claimed in claim 1, wherein said halodifluoromethane corresponds to the following formula (I):
   HXCF2 (I); and
wherein in said formula (I), X represents a chlorine, bromine, or iodine atom.

3. The process as claimed in claim 1, wherein said halodifluoromethane is chlorodifluoromethane.

4. The process as claimed in claim 1, wherein said source of cyanide anions is sodium cyanide or potassium cyanide.

5. The process as claimed in claim 1, wherein said reaction is carried out in the presence of a base, said base being an alkali metal hydroxide.

6. The process as claimed in claim 5, wherein said base used is in the form of an aqueous solution of said alkali metal hydroxide having a concentration between 5% and 50% by weight.

7. The process as claimed in claim 1, wherein said reaction is performed at a temperature between 20° C. and 150° C.

8. The process as claimed in claim 1, wherein said reaction is carried out in the presence of a base; wherein said cyanide source and said base are mixed to form a reaction medium; wherein said halodifluoromethane is then injected into said reaction medium; and wherein, at the end of said reaction, the difluoroacetonitrile formed, present in an organic phase, is recovered.

9. A process for preparing difluoroacetic acid, salts thereof or esters thereof, comprising the process for preparing difluoroacetonitrile from said halodifluoromethane as claimed in claim 1 as a first step, followed by a hydrolysis operation.

10. The process as claimed in claim 9, wherein difluoroacetic acid is prepared by hydrolysis, in an acid medium, of the difluoroacetonitrile obtained in said first step.

11. The process as claimed in claim 9, wherein difluoroacetic acid is prepared by hydrolysis of the difluoroacetonitrile obtained in said first step, in a basic medium.

12. The process as claimed in claim 9, wherein an ester of difluoroacetic acid is prepared by hydrolysis of the difluoroacetonitrile obtained in said first step, in an acid medium and in the presence of an alcohol.

13. The process as claimed in claim 9, wherein difluoroacetamide is prepared by a controlled hydrolysis of the difluoroacetonitrile obtained in said first step, in an acid medium.

14. The process as claimed in claim 13, wherein said hydrolysis is carried out using a strong acid; and wherein the amount of said strong acid used is such that the ratio between the number of moles of acid expressed as H+ ions and the number of said difluoroacetonitrile varies between 0.05 and 1.

15. A process for preparing a salt of difluoroacetic acid, comprising reacting a halodifluoromethane and a source of cyanide anions in a basic aqueous medium, in the presence of an amount of a base necessary both for carrying out a cyanation reaction and a hydrolysis reaction.

16. The process as claimed in claim 15, wherein said halodifluoromethane is chlorodifluoromethane.

17. The process as claimed in claim 15, wherein said source of cyanide anions is sodium cyanide or potassium cyanide.

18. The process as claimed in claim 15, wherein said base is an alkali metal hydroxide.

19. The process as claimed in claim 18, wherein said base used is in the form of an aqueous solution of said alkali metal hydroxide having a concentration between 5% and 50% by weight.

20. The process as claimed in claim 16, wherein the amount of said base used is such that the ratio between the number of moles of said base expressed as OH— and the number of moles of said chlorodifluoromethane varies between 2 and 5.

21. The process as claimed in claim 15, wherein the temperature for reacting said halodifluoromethane and said source of cyanide anions is between 100° C. and 120° C.

* * * * *